US008882774B2

(12) United States Patent
Malinin

(10) Patent No.: US 8,882,774 B2
(45) Date of Patent: Nov. 11, 2014

(54) INSTRUMENTATION FOR THE PREPARATION AND TRANSPLANTATION OF OSTEOCHONDRAL ALLOGRAFTS

(75) Inventor: Theodore I. Malinin, Key Biscayne, FL (US)

(73) Assignee: Biomet Sports Medicine, LLC, Warsaw, IN (US)

(*) Notice: Subject to any disclaimer, the term of this patent is extended or adjusted under 35 U.S.C. 154(b) by 678 days.

(21) Appl. No.: 11/677,414

(22) Filed: Feb. 21, 2007

(65) Prior Publication Data
US 2007/0135917 A1 Jun. 14, 2007

Related U.S. Application Data

(62) Division of application No. 11/259,749, filed on Oct. 26, 2005, now Pat. No. 7,371,260.

(51) Int. Cl.
A61B 17/88 (2006.01)
A61B 17/16 (2006.01)
(Continued)

(52) U.S. Cl.
CPC ........... A61B 17/1615 (2013.01); A61F 2/4601 (2013.01); A61F 2/30756 (2013.01);
(Continued)

(58) Field of Classification Search
USPC .................. 606/79–85, 86 R, 87, 96–98, 104
See application file for complete search history.

(56) References Cited

U.S. PATENT DOCUMENTS 43,909 A 8/1864 Hair
493,730 A 3/1893 MacKenzie
(Continued)

FOREIGN PATENT DOCUMENTS

DE 19503504 3/1996
WO WO-9106246 5/1991
WO WO-2004103224 12/2004

OTHER PUBLICATIONS

Chu et al., "Articular Cartilage Transplantation: Clinical Results in the Knee," Clinical Orthopaedics and Related Research, No. 360, pp. 159-168 (Mar. 1999).

(Continued)

Primary Examiner — Michael T Schaper
(74) Attorney, Agent, or Firm — Harness, Dickey

(57) ABSTRACT

Procedures and instruments for preparing and transplanting osteochondral allograft plugs to a host bone to repair an articular cartilage defect. An allograft bone plug having a cartilage plate and cancellous bone tissue attached thereto is removed from a donor bone. The allograft plug is further shaped by removing or cutting away cancellous bone tissue to form a cancellous stalk extending from the cartilage plate. At the recipient site of the host bone, a cutout is formed corresponding in shape to the allograft plug. The allograft plug is inserted into the cutout such that the cancellous stalk is retained in the host bone and the cartilage plate aligns with the condyle surface of the host bone.

22 Claims, 12 Drawing Sheets

(51) Int. Cl.
  *A61B 17/17* (2006.01)
  *A61F 2/30* (2006.01)
  *A61F 2/28* (2006.01)
  *A61F 2/46* (2006.01)
  *A61B 17/06* (2006.01)
  *A61B 17/28* (2006.01)
  *A61B 17/92* (2006.01)
  *A61F 2/38* (2006.01)

(52) U.S. Cl.
  CPC ....... *A61B 17/06166* (2013.01); *A61B 17/1675* (2013.01); *A61F 2002/30772* (2013.01); *A61B 2017/2837* (2013.01); *A61F 2230/0086* (2013.01); *A61F 2002/30233* (2013.01); *A61F 2230/0019* (2013.01); *A61F 2002/30153* (2013.01); *A61F 2002/30156* (2013.01); *A61F 2230/0023* (2013.01); *A61F 2002/30971* (2013.01); *A61B 2017/922* (2013.01); *A61F 2230/0093* (2013.01); *A61F 2/28* (2013.01); *A61F 2/4644* (2013.01); *A61F 2002/2839* (2013.01); *A61F 2230/0089* (2013.01); *A61B 17/282* (2013.01); *A61F 2230/0069* (2013.01); *A61B 17/1604* (2013.01); *A61F 2/3859* (2013.01); *A61F 2002/30299* (2013.01); *A61F 2/4618* (2013.01); *A61F 2002/3021* (2013.01); *A61F 2002/4649* (2013.01); *A61F 2002/30113* (2013.01); *A61F 2230/0006* (2013.01); *A61F 2002/30273* (2013.01); *A61F 2002/30764* (2013.01); *A61F 2002/4681* (2013.01); *A61F 2002/30275* (2013.01); *A61F 2230/0067* (2013.01)
  USPC ............... 606/86 R; 606/80; 606/96; 606/104

(56) References Cited

U.S. PATENT DOCUMENTS

| | | | |
|---|---|---|---|
| 1,911,873 A | 5/1933 | Balton | |
| 2,573,462 A | 10/1951 | Lindsey | |
| 2,591,516 A | 4/1952 | Darnell | |
| 3,835,849 A * | 9/1974 | McGuire | 606/96 |
| 3,848,601 A | 11/1974 | Ma et al. | |
| 3,875,936 A * | 4/1975 | Volz | 606/309 |
| 4,007,732 A | 2/1977 | Kvavle et al. | |
| 4,010,737 A | 3/1977 | Vilaghy et al. | |
| 4,059,115 A | 11/1977 | Jumashev et al. | |
| 4,177,797 A | 12/1979 | Baylis et al. | |
| 4,341,206 A * | 7/1982 | Perrett et al. | 606/80 |
| 4,416,278 A | 11/1983 | Miller | |
| 4,444,180 A * | 4/1984 | Schneider et al. | 606/96 |
| 4,528,980 A * | 7/1985 | Kenna | 606/80 |
| 4,565,192 A | 1/1986 | Shapiro | |
| 4,627,853 A | 12/1986 | Campbell et al. | |
| 4,649,918 A | 3/1987 | Pegg et al. | |
| 4,741,651 A | 5/1988 | Despres | |
| 4,782,833 A | 11/1988 | Einhorn et al. | |
| 4,904,259 A | 2/1990 | Itay | |
| 4,913,143 A | 4/1990 | Oloff et al. | |
| 4,936,313 A | 6/1990 | Burkhardt et al. | |
| 5,041,117 A | 8/1991 | Engelhardt | |
| 5,053,050 A | 10/1991 | Itay | |
| 5,139,520 A | 8/1992 | Rosenberg | |
| 5,152,763 A | 10/1992 | Johnson | |
| 5,197,967 A | 3/1993 | Wilson | |
| 5,211,647 A | 5/1993 | Schmieding | |
| 5,269,786 A | 12/1993 | Morgan | |
| 5,320,115 A | 6/1994 | Kenna | |
| 5,320,626 A | 6/1994 | Schmieding | |
| 5,341,816 A | 8/1994 | Allen | |
| 5,397,357 A | 3/1995 | Schmieding et al. | |
| 5,415,651 A | 5/1995 | Schmieding | |
| 5,423,823 A | 6/1995 | Schmieding | |
| 5,489,310 A * | 2/1996 | Mikhail | 623/19.11 |
| 5,496,326 A | 3/1996 | Johnson | |
| 5,513,662 A | 5/1996 | Morse et al. | |
| 5,540,692 A | 7/1996 | Tidwell | |
| 5,562,669 A | 10/1996 | McGuire | |
| 5,603,716 A | 2/1997 | Morgan et al. | |
| 5,655,546 A | 8/1997 | Halpern | |
| 5,733,289 A | 3/1998 | Seedhom et al. | |
| 5,782,835 A | 7/1998 | Hart et al. | |
| 5,785,714 A | 7/1998 | Morgan et al. | |
| 5,817,098 A | 10/1998 | Albrektsson et al. | |
| 5,827,288 A | 10/1998 | Umber et al. | |
| 5,865,834 A | 2/1999 | McGuire | |
| 5,885,293 A | 3/1999 | McDevitt | |
| 5,895,390 A * | 4/1999 | Moran et al. | 606/96 |
| 5,904,717 A | 5/1999 | Brekke et al. | |
| 5,918,604 A | 7/1999 | Whelan | |
| 5,919,196 A | 7/1999 | Bobic et al. | |
| 6,007,496 A | 12/1999 | Brannon | |
| 6,017,348 A | 1/2000 | Hart et al. | |
| 6,110,178 A | 8/2000 | Zech et al. | |
| 6,146,385 A | 11/2000 | Torrie et al. | |
| 6,179,839 B1 | 1/2001 | Weiss et al. | |
| 6,179,871 B1 | 1/2001 | Halpern | |
| 6,187,329 B1 | 2/2001 | Agrawal et al. | |
| 6,231,577 B1 | 5/2001 | Canedy | |
| 6,242,247 B1 | 6/2001 | Rieser et al. | |
| 6,280,447 B1 | 8/2001 | Marino et al. | |
| 6,305,379 B1 | 10/2001 | Wolfinbarger, Jr. | |
| 6,358,253 B1 | 3/2002 | Torrie et al. | |
| 6,375,658 B1 | 4/2002 | Hangody et al. | |
| 6,387,693 B2 | 5/2002 | Rieser et al. | |
| 6,395,011 B1 | 5/2002 | Johanson et al. | |
| 6,442,814 B1 | 9/2002 | Landry et al. | |
| 6,458,144 B1 | 10/2002 | Morris et al. | |
| 6,488,033 B1 | 12/2002 | Cerundolo | |
| 6,528,052 B1 | 3/2003 | Smith et al. | |
| 6,530,928 B1 | 3/2003 | Frei et al. | |
| 6,557,226 B1 | 5/2003 | Landry et al. | |
| 6,591,581 B2 | 7/2003 | Schmieding | |
| 6,592,588 B1 | 7/2003 | Bobic et al. | |
| 6,607,534 B2 | 8/2003 | Bonutti | |
| 6,613,054 B2 | 9/2003 | Scribner et al. | |
| 6,685,709 B2 | 2/2004 | Sklar | |
| 6,696,073 B2 | 2/2004 | Boyce et al. | |
| 6,727,224 B1 | 4/2004 | Zhang et al. | |
| 6,740,484 B1 | 5/2004 | Khirabadi et al. | |
| 6,796,977 B2 | 9/2004 | Yap et al. | |
| 6,835,377 B2 | 12/2004 | Goldberg et al. | |
| 6,852,114 B2 | 2/2005 | Cerundolo | |
| 6,962,592 B2 | 11/2005 | Gatturna et al. | |
| 7,231,815 B2 * | 6/2007 | Kanare | 73/73 |
| 7,241,316 B2 | 7/2007 | Evans et al. | |
| 7,347,130 B2 | 3/2008 | Pham et al. | |
| 2001/0027322 A1 | 10/2001 | Bowman | |
| 2001/0039455 A1 | 11/2001 | Simon et al. | |
| 2002/0022847 A1 | 2/2002 | Ray et al. | |
| 2002/0082704 A1 | 6/2002 | Cerundolo | |
| 2002/0095214 A1 | 7/2002 | Hyde | |
| 2003/0009218 A1 | 1/2003 | Boucher et al. | |
| 2003/0130662 A1 | 7/2003 | Michelson | |
| 2003/0212435 A1 | 11/2003 | Gold et al. | |
| 2004/0106928 A1 | 6/2004 | Ek | |
| 2004/0162622 A1 | 8/2004 | Simon et al. | |
| 2004/0186482 A1 * | 9/2004 | Kolb et al. | 606/96 |
| 2004/0210227 A1 * | 10/2004 | Trail et al. | 606/73 |
| 2004/0230303 A1 | 11/2004 | Gomes et al. | |
| 2005/0064042 A1 | 3/2005 | Vunjak-Novakovic et al. | |
| 2005/0222576 A1 | 10/2005 | Kick et al. | |
| 2006/0142775 A1 | 6/2006 | Heneberry et al. | |
| 2007/0093896 A1 | 4/2007 | Malinin | |
| 2007/0135918 A1 | 6/2007 | Malinin | |
| 2007/0135928 A1 | 6/2007 | Malinin | |
| 2007/0276506 A1 | 11/2007 | Troxel | |
| 2009/0093853 A1 | 4/2009 | Missos et al. | |

OTHER PUBLICATIONS

Convery et al., "Long-term Survival of Chondrocytes in an Osteochondral Articular Cartilage Allograft," *Journal of Bone and Joint Surgery*, vol. 78-A, No. 7, pp. 1082-1088 (Jul. 1996).

(56) References Cited

OTHER PUBLICATIONS

Hangody et al., "Autologous Osteochondral Mosaicplasty for the Treatment of Full-Thickness Defects of Weight-Bearing Joints," *Journal of Bone and Joint Surgery*, vol. 85-a, Supp. 2, pp. 25-32 (2003).

Malinin et al., "Hypothermic Storage and Cryopreservation of Cartilage: an Experimental Study," *Clinical Orthopedics and Related Research*, No. 197, pp. 15-26 (Jul.-Aug. 1985).

Malinin et al, "Articular Cartilage Nutrition is Mediated by Subchondral Bone: a Long-Term Autograft Study in Baboons," *Osteoarthritis and Cartilage*, vol. 8, pp. 483-491, (2000).

Williams et al., "Prolonged Storage Effects on the Articular Cartilage of Fresh Human Osteochondral Allografts," *Journal of Bone and Joint Surgery*, vol. 85-A, No. 11, pp. 2111-2120 (Nov. 2003).

Restriction Requirement, U.S. Appl. No. 11/259,749 (Jan. 5, 2007).

"Matrices for Cartilage Repair," Coutes, et al., published in Clinical Orthopaedics & Related Research, No. 391S pp. 271-S279, copyright 2001 Lippincott Williams & Wilkins, Inc.

"Techniques for ACL Reconstruction with Multi-Trac™ Drill Guide," available by 2000.

Acufex Microsurgical, Inc., "Endoscopic Technique for ACL Reconstruction with Pro-Trac Tibial Guide: Endobutton Fixation," available by 2000.

Arthrex, "Osteochondral Autograft Transfer System (OATS), Key Words: Chondral defects, osteochondral cylinder transplants, arthroscopic technique, chronic ACL deficiency" © Arthrex Inc.,1996 (1 page).

Arthrex, Osteochondral Autograft Transfer System (OATS)™, "Surgical Technique," 1996 (pages 1-24).

Arthrotek® OCD System, Osteochondral Defect Surgical Technique, brochure, © 1999 (4 pages).

Gross, M.D., Allan, "Cartilage Resurfacing Filling Defects," The Journal of Arthroplasty vol. 18 No. 3 Suppl. 1 (2003) pp. 14-17.

Hangody, et al., "Arthroscopic autogenous osteochondral mosaicplasty for the treatment of femoral condylar articular defects, A preliminary report," Knee, Surg, Sports Traumatol. Arthrosc (1997) © Springer-Verlag 1997 5:262-267.

Hangody, M.D., et al., "MosaicPlasty™ Osteochondral Grafting Technique Guide", Smith & Nephew Endoscopy, © 1996.

Innovasive Cor™ System, © 1997 Innovasive Devices, Inc. (2 pages).

Instrument Makar, Inc., "Bone Grafters Surgical Technique," Dec. 1995.

Instrument Makar, Inc.,"New Directions in Arthroscopic Innovation," 1991 Catalogue.

Jakob, M.D., Roland, et al., "Autologous Osteochondral grafting in the Knee: Indication, Results, and Reflections," Clinical Orthopaedics and Related Research No. 401, (2002) pp. 170-184.

Malinin, T., M.D., Human Cadaver Femoral Head Homografts for Anterior Cervical Spine Fusions, Reprinted from Surgical Neurology, vol. 7, No. 4, Apr. 1977, Copyright, © 1977.

Malinin, T.I., "University of Miami Tissue Bank: Collection of Postmortem Tissues for Clinical Use and Laboratory Investigation", From the Departments of Surgery and Pathology, University of Miami School of Medicine and the Veterans Administration Hospital, Translantation Proceedings, vol. VIII, No. 2, Supplement 1 (Jun.), 1976 (pp. 53-58).

Szerb, M.D., et al., "Mosaicplasty, Long-Term Follow-Up," Bulletin of the Hospital for Joint Diseases, vol. 63, Nos. 1 & 2 (2005), pp. 54-62.

Arthrex, Inc., Osteochondral Autograft Transfer System (OATS), "Surgical Technique," (pp. 1-22) 1998.

Christel, P., et al., "Osteochondral Grafting Using Mosaicplasty Technique," www.maitrise-orthop.com/corpusmaitri/orthopaedic/mo76_mosaicplasty/index.shtml (23 pages) printed Mar. 23, 2005.

Matsusue, Y., et al., "Arthroplasty using Mosaicplasty," Clinical Calcium, vol. 12, No. 1 (pp. 66-69) 2002.

\* cited by examiner

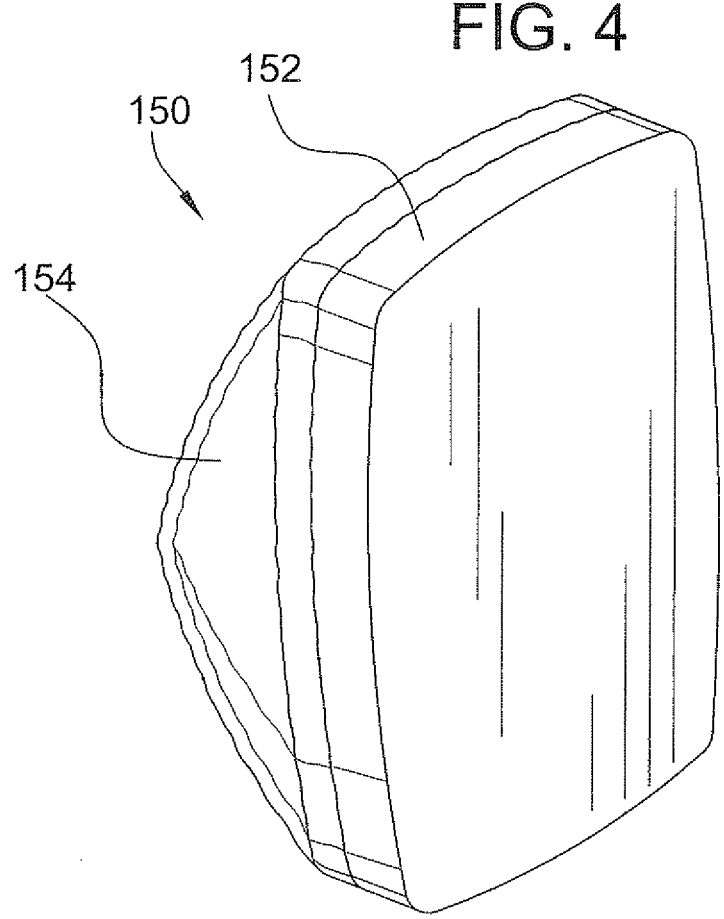
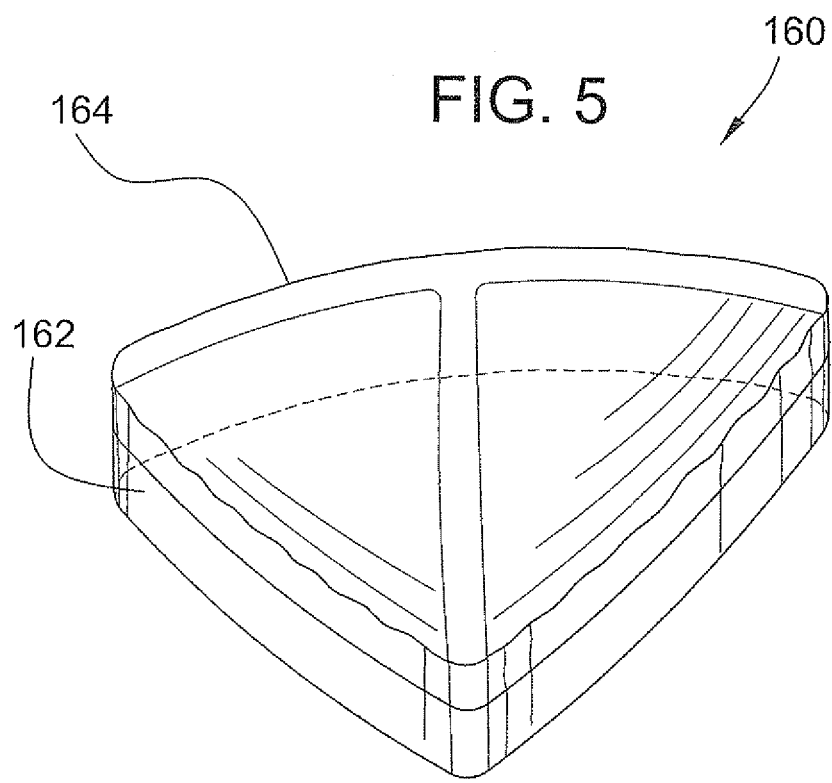

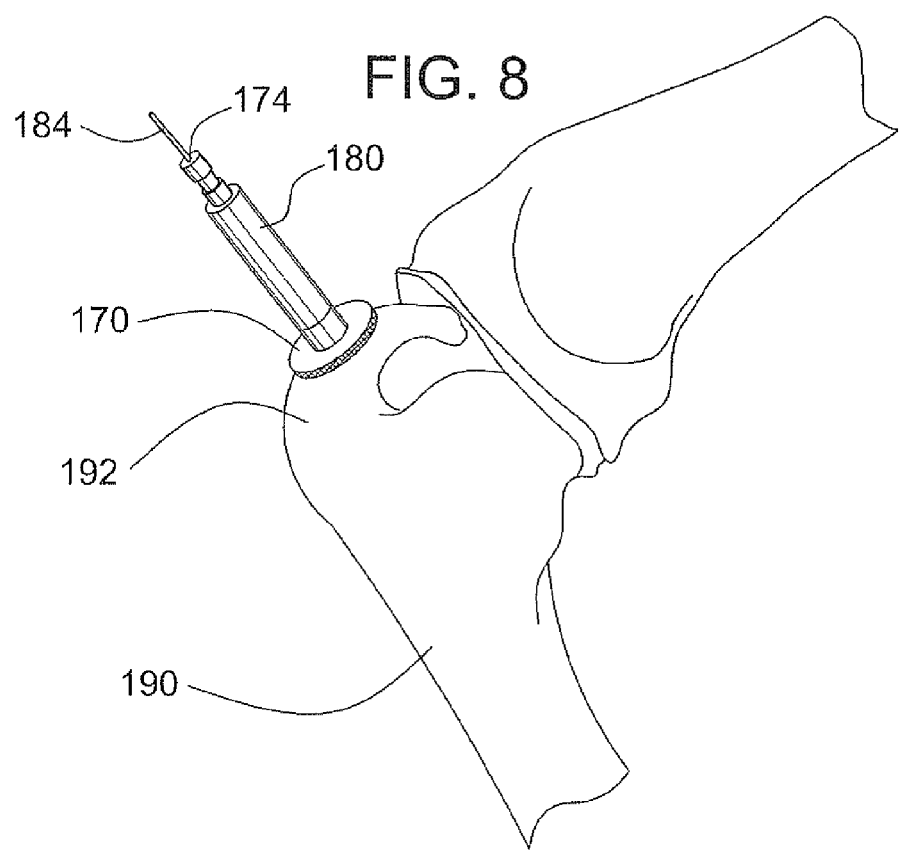
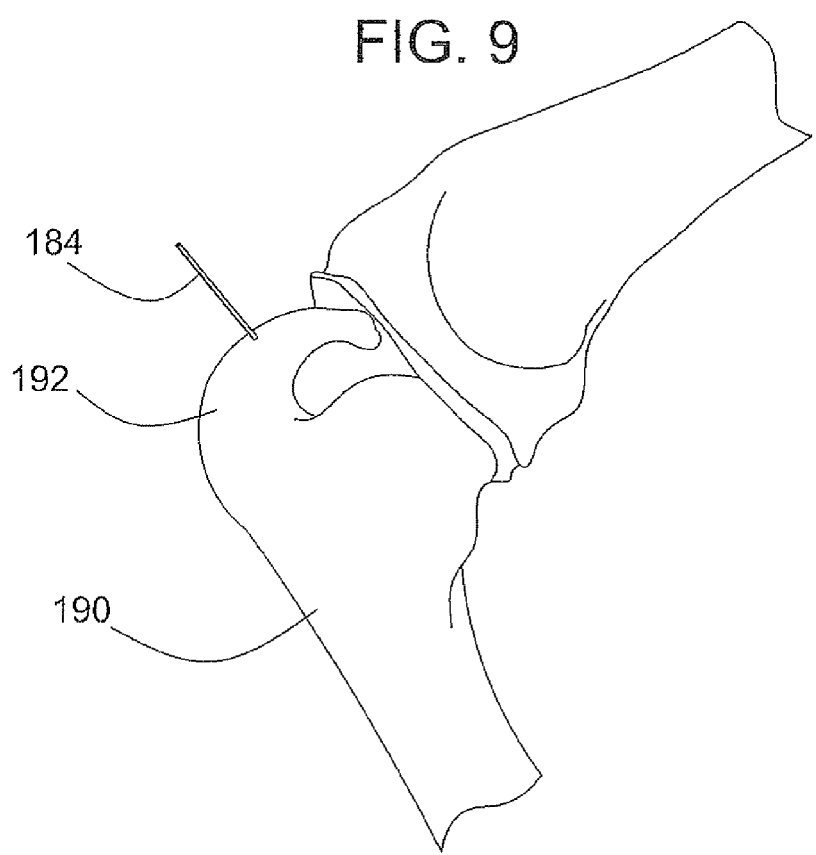

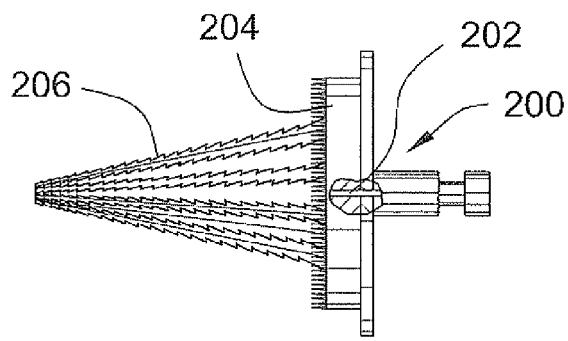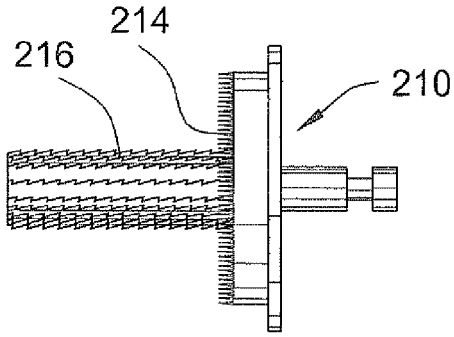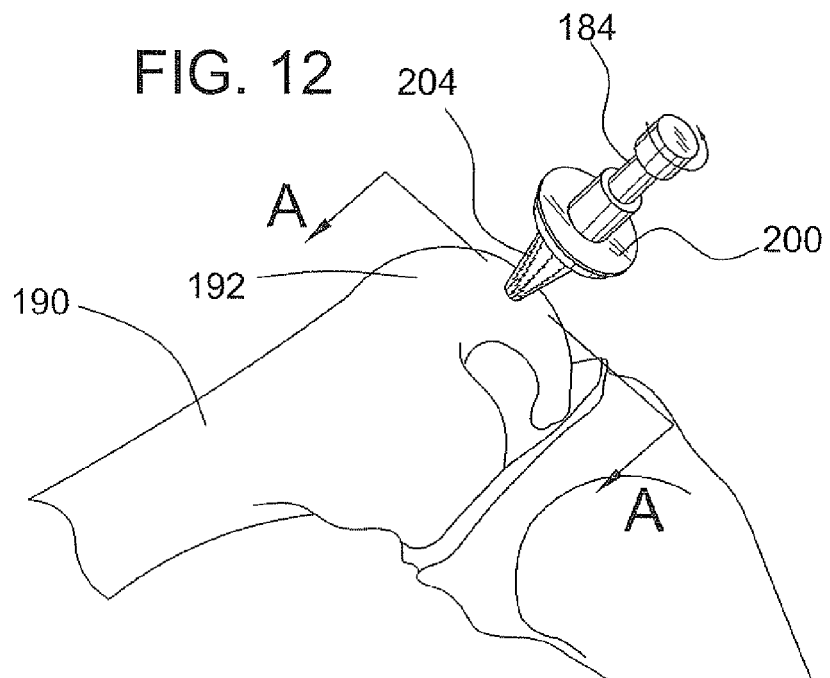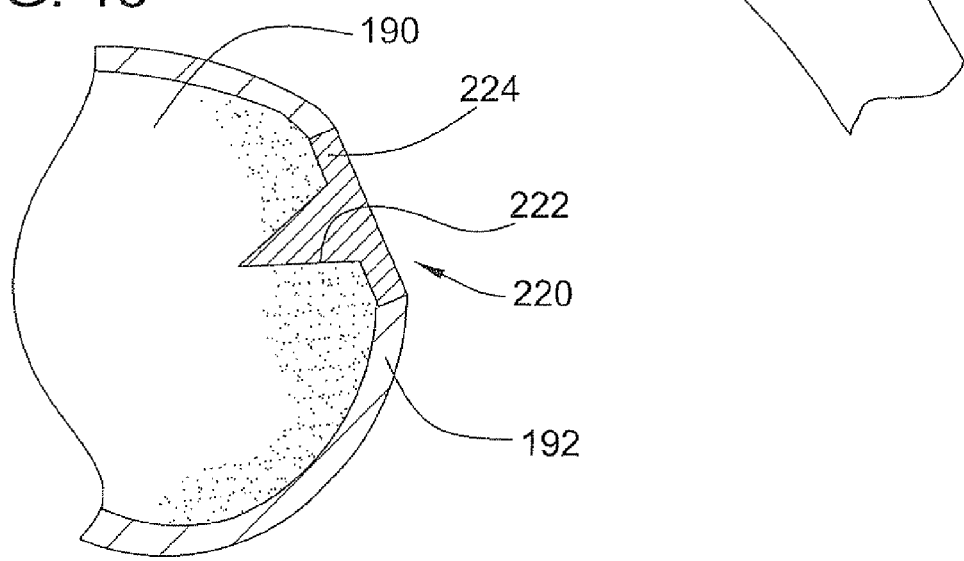

INSTRUMENTATION FOR THE PREPARATION AND TRANSPLANTATION OF OSTEOCHONDRAL ALLOGRAFTS

CROSS-REFERENCE TO RELATED APPLICATIONS

This patent application is a divisional application of copending U.S. patent application Ser. No. 11/259,749, filed Oct. 26, 2005, the disclosure of which is herein incorporated by reference in its entirety.

BACKGROUND OF THE INVENTION

In humans and many other animals, cartilage is present on the surface of bones that form articular joints to facilitate articulation of the joint and protect and cushion the bones. However, defects may develop in the cartilage from various causes such as abrupt trauma or prolonged wear. A number of techniques have been attempted to treat such cartilage defects. One such technique is the transplantation of fresh osteochondral allografts.

In this procedure, an allograft plug, also known as a osteochondral plug or core, is harvested from a condyle or rounded joint-forming portion of a donor bone. Intact on the surface of the allograft plug, on a portion of the bone known as the cartilage plate, is healthy cartilage. The allograft plug may also have attached to the cartilage plate cancellous tissue, which is the porous inner material that is present in many bones. In the recipient patient, the cartilage defect and the corresponding portion of underlying bone are cutaway and removed from the joint. The allograft plug is then inserted and attached to the cutaway portion so that the cartilage plate and healthy cartilage of the allograft plug align with the cartilage on the surface of the host bone.

One problem that arises with osteochondral allografts is that the recipient may adversely respond or reject the allograft plug. This can happen primarily because of the antigenic material contained in the cancellous bone of the allograft plug. Occurrence of such an adverse response may result in the recipient site reforming or healing in such a manner that the allograft plug becomes walled off from the host bone thereby delaying or preventing incorporation of the allograft. In addition, physically attaching and securing the allograft plug to the recipient site presents difficulties.

BRIEF SUMMARY OF THE INVENTION

The invention provides methods and instruments for preparing and transplanting osteochondral allografts to repair articular cartilage defects. According to one aspect of the invention, an allograft plug having a cartilage plate and cancellous bone tissue attached thereto is removed from a donor bone. The allograft plug is further shaped by removing or cutting away cancellous bone tissue to form a cancellous stalk extending from the cartilage plate. The formed cancellous stalk can have any suitable shape including cylindrical, conical, and rectilinear. According to another aspect of the invention, in what will become the host bone of the patient, a recipient site is prepared by forming a cutout corresponding to the cartilage defect. The shape of the cutout generally corresponds to the shape of a provided allograft plug from which cancellous material has been removed to form a cancellous stalk. The allograft plug is inserted into the cutout such that the cancellous stalk is retained in the host bone and the cartilage plate aligns with the condyle surface of the host bone. Removing and shaping the allograft plug can be performed separately or together with preparing a recipient site by forming a cutout and inserting the allograft plug into the cutout.

To prepare the recipient site, a template can be attached to the host bone in a location corresponding to the cartilage defect. In an aspect of the invention, the template can include a guide aperture disposed therein. To facilitate alignment of subsequent operations, an elongated guide pin is inserted through the guide aperture and into the host bone. Cannulated drill bits having the desired shape can be slid over the guide pin and driven into the host bone to form the shaped cutout. In another aspect of the invention, the template can include a plurality of cut slots disposed therein. A cutting device can then be inserted through the cut slots and into the host bone to form the shaped cutout.

To remove and shape the allograft plug from the donor site, a second template specially adapted to attach to the donor bone can be used. One advantage of employing a template to remove the allograft plug is that template may facilitate simultaneous shaping of the allograft plug at the time of removal. In other embodiments, the allograft plug can initially be a piece of cylindrically or otherwise shaped bone material removed from the donor bone and subsequently shaped to produce the finished allograft plug.

It should be recognized that various aspects of the invention may also be applicable to preparing and transplanting an osteochondral autograft plug, a process which involves removing a plug from a first location and transplanting the plug into a second location within the same patient.

The invention provides one or more of the following advantages: An advantage of the invention is that it provides a osteochondral allograft plug that has a reduced amount of cancellous tissue and is therefore less likely to be rejected by a recipient. Another advantage is that it provides a specially shaped osteochondral allograft plug that can be fit and anchored into a correspondingly shaped cutout at the recipient site. These and other advantages and features of the invention will be apparent from the detailed description and the accompanying drawings.

BRIEF DESCRIPTION OF THE SEVERAL VIEWS OF THE DRAWINGS

FIG. 4 is a perspective view of another embodiment of an allograft plug having a rectangular shape.

FIG. 5 is a perspective view of another embodiment of an allograft plug having a triangular shape.

FIG. 8 is a perspective view of the template of FIG. 6 attached to the condyle of host bone in accordance with an embodiment of the invention, the handle being engaged to the template and a guide pin being inserted through the template FIG. 9 is a perspective view of the guide pin inserted into the condyle of the host bone after removal of the template.

FIG. 10 is a side elevational view of another embodiment of a cannulated drill bit for forming a cutout in a recipient site in accordance with an embodiment of the invention, the drill bit having a counter-bore forming element and a conical cutting body with a central cannula shown in cutaway.

FIG. 11 is a side elevational view of another cannulated drill bit for forming a cutout in a recipient site in accordance with an embodiment of the invention, the drill bit having a counter-bore forming element and a cylindrical cutting body.

FIG. 12 is a perspective view of the drill bit of FIG. 9 being driven into the condyle of the host bone to form the cutout.

FIG. 13 is a cross-sectional view taken generally along line A-A of FIG. 12 illustrating cutout formed into a recipient site of a condyle of a host bone.

DETAILED DESCRIPTION OF THE INVENTION

Figure 1:
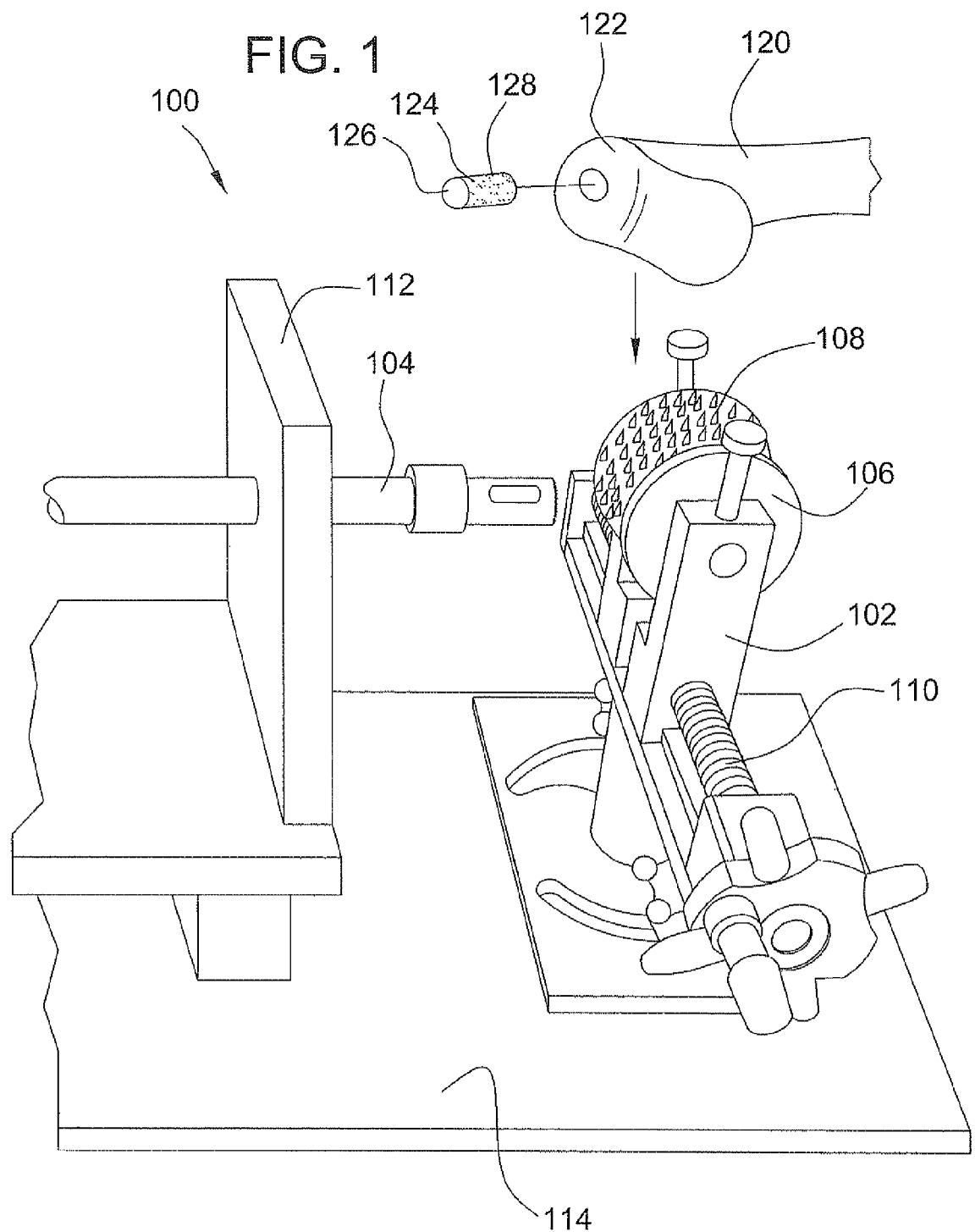
FIG. 1 is a perspective view of a device for removing from a donor bone a transplantable osteochondral allograft plug for repairing a cartilage defect.

Now referring to the drawings, wherein like reference numbers refer to like elements, there is illustrated various processes and instruments for preparing and transplanting an osteochondral allograft in accordance with the various embodiments of the invention. Referring first to FIG. 1, there is shown a device 100 suitable for cutting and forming a cylindrically shaped allograft plug 124 from a donor bone 120 in accordance with one aspect of the invention. The device 100 itself includes a clamp assembly 102 and a tubular crown saw 104. The clamp assembly 102 includes two vertically extending clamp pads 106, 108, that can be moved with respect to each other by rotation of a linear screw mechanism 110. The crown saw 104 is directed towards and linearly movable with respect to the clamp assembly 102. To align the clamp assembly 102 and crown saw 104, the crown saw can pass through a vertical alignment plate 112 joined to a base 114 onto which the clamp assembly is also mounted.

To produce an allograft plug, a donor bone 120 or a portion thereof having on its surface healthy cartilage is received between the clamp pads 106, 108 and the clamp pads are moved together to grasp and hold the donor bone in alignment with the crown saw 104. Preferably, the donor bone 120 can be received in the clamp assembly 102 such that a condyle 122 corresponding to a donor site on the donor bone 120 is positioned towards the crown saw 104. The rotating tubular crown saw 104 is moved towards and into the donor site 122 to form a cylindrical cut into the donor bone 120, after which the crown saw can be removed. The cylindrically shaped bone material 124 produced by the cylindrical cut and that will correspond to the allograft plug can then be removed from the remainder of the donor bone 120 by, for example, transecting the donor bone with a saw or by propagating a crack through the donor bone with a tamp or similar device.

The removed cylindrical shaped bone material 124 has a cartilage plate 126 corresponding to the outer surface of the donor bone 120 and on which healthy cartilage is located. Extending from the cartilage plate 126 is cancellous bone tissue 128 from the interior portion of the donor bone 120. As will be appreciated by those of skill in the art, when making the cut into the donor site 122, the donor bone 120 and the crown saw 104 are preferably arranged so that the contour of the cartilage plate 126 corresponds to the portion of the host bone which is to be repaired.

Once the cylindrically cut bone material has been removed, it can be shaped by any variously suitable subsequent shaping operation to remove cancellous bone tissue and form a cancellous stalk extending from the cartilage plate. Removing cancellous bone tissue results in the cancellous stalk having a reduced cross section compared to the cross-section of the cartilage plate.

Because the cancellous bone tissue on the allograft plug could contain antigenic material, reducing the amount of cancellous bone tissue transplanted to the host reduces the possibility of an adverse reaction within the host. Another advantage of shaping the allograft plug to form a cancellous stalk is that the stalk provides an anchor-like structure that assists in anchoring the allograft plug into a recipient site on the host bone. A related advantage is that, by removing cancellous tissue from the cancellous stalk, the amount of cancellous tissue that must be accommodated by the host bone during transplantation is reduced. Accordingly, the size of the cutout that must be formed into a recipient site on the host bone is likewise reduced thereby requiring less trauma to the host bone.

The finished allograft plug can have any suitable shape. For example, referring to FIG. 2, there is illustrated an allograft plug 130 having a circular cartilage plate 132 and a cylindrical cancellous stalk 134 of cancellous bone tissue extending therefrom. The cartilage plate 132 has a generally circular perimeter of a first diameter and includes healthy cartilage from the donor intact on subchondral bone tissue 136. On the underside of the cartilage plate 132 there may also be a thin layer of cancellous bone tissue 138 which corresponds to the first diameter. The cylindrically shaped cancellous stalk 134 extends from the thin layer of cancellous bone tissue 138 and has a second perimeter or second diameter reduced in size with respect to the first diameter. The reduction in size of the second perimeter compared to the first perimeter is the result of removing cancellous bone tissue to form the stalk. Preferably, the circular cartilage plate 132 and the cylindrical cancellous stalk 134 are coaxial.

Figure 3:
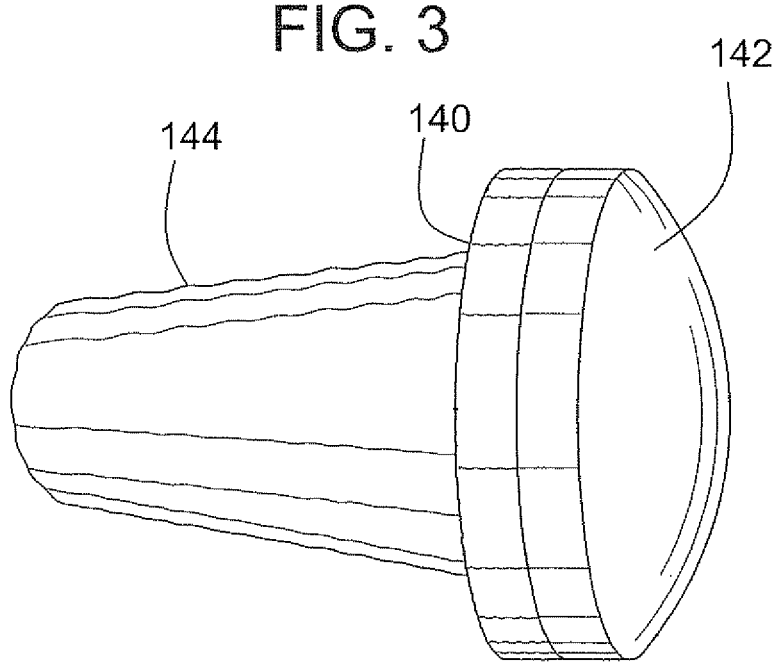
FIG. 3 is a perspective view of another embodiment of an allograft plug having a cartilage plate and a conical cancellous stalk.

Referring to FIG. 3, there is illustrated another embodiment of an allograft plug 140 having circular cartilage plate 142 and a generally conical cancellous stalk 144 extending therefrom. The cartilage plate 142 again has a first perimeter of a given first diameter while the concial perimeter of the cancellous stalk tapers so as to progressively reduce in diameter as the stalk extends from the cartilage plate. Preferably, the circular cartilage plate 142 and the conical cancellous stalk are coaxial. In other embodiments, the cancellous stalk may have a stepped shape with each step having a reduced perimeter or diameter compared to the first perimeter of the cartilage plate.

Referring to FIG. 4, there is illustrated another embodiment of an allograft plug 150 having rectangular cartilage plate 152 with a tapering or rectangular pyramid-shaped cancellous stalk 154. As will be appreciated, the tapering of the cancellous stalk 154 results in a progressive reduction of its cross-section with respect to the cross-section of the rectangular cartilage plate 152. Referring to FIG. 5, there is illustrated an allograft plug 160 having a triangular cartilage plate 162 and a tapering triangular pyramid-shaped cancellous stalk 164 extending therefrom. In other embodiments, the rectangular and triangular cartilage plates can have respective rectangular and triangular cross-sectioned stalks extending therefrom.

Figure 6:
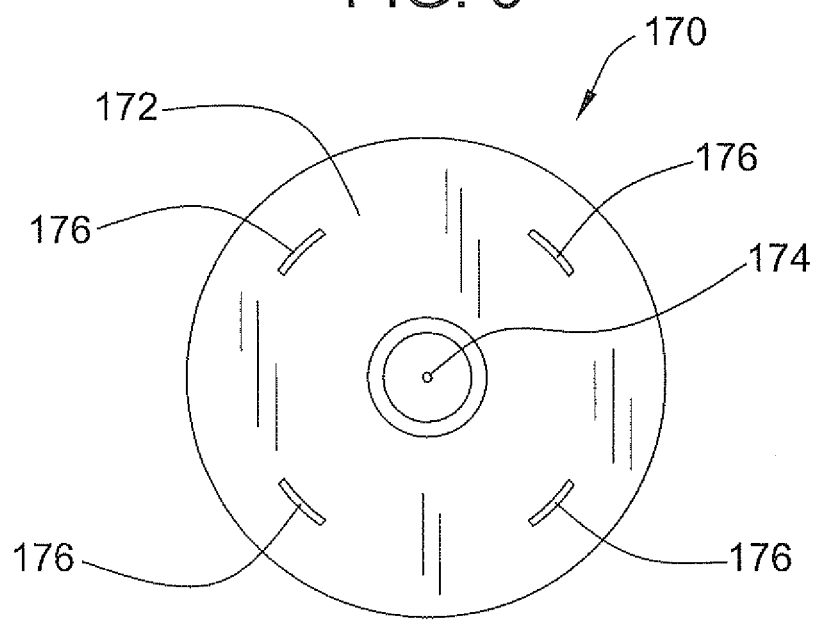
FIG. 6 is a front elevational view of a template for preparing a recipient site in accordance with the teachings of the invention, the template including a central guide aperture.
Figure 7:
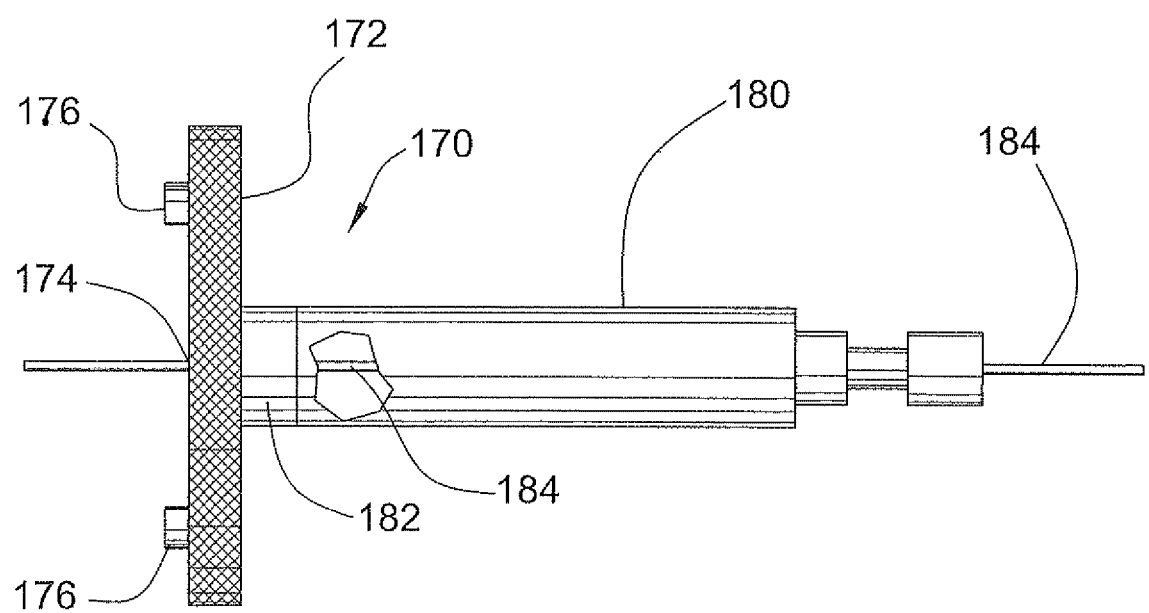
FIG. 7 is a side elevational view of the template shown in FIG. 6 and further illustrating a detachable handle engaged to the template.

To prepare a recipient site in a host bone for receiving the allograft plug, special instruments can be used to form a cutout corresponding in shape to the allograft plug. Such special tools can include, for example, a template 170 as illustrated in FIGS. 6 and 7. The template 170 includes a flat, circular template plate 172 through the center of which is disposed a guide aperture 174. From one surface of the template plate 172 there projects a short distance a plurality of sharp teeth 176. The teeth 176 are preferably arranged in a circular pattern concentric with the circular template plate 172. To enable manipulation of the template 170, the template preferably also includes a detachable handle 180 that engages a corresponding engagement structure 182 on the opposite surface of the plate 172 from which the teeth 176 project. The handle 180 and plate 172 can be engaged by, for example, a twist lock mechanism. In various embodiments, the guide aperture 174 can continue through the detachable handle 180 as well. The guide aperture 174 is adapted to receive a guide pin 184 in a sliding fit such that the guide pin 184 can be inserted through the center of the plate 172.

When preparing a recipient site with the template, referring to FIG. 8, a joint such as a knee joint of the patient being treated is first manipulated to expose the cartilage defect on the surface of a condyle 192 of a host bone 190. Once the cartilage defect is suitably exposed, the template 170 is attached via the sharp, projecting teeth to the condyle 192 at a location corresponding to the defect. Preferably, to minimize damage, the circular pattern of the teeth projecting from the template corresponds to the area of the defect. Once the template 170 is attached, the detachable handle 180 can be removed and the guide pin 184 inserted through the guide aperture 174 and into the host bone 190 at the location of the defect. Once the guide pin 184 is driven into the host bone 190, the handle 180 can be reattached to the template 170 and the template pull over the guide pin and removed from the condyle 192. In other embodiments, the guide pin can be inserted with the handle remaining attached to the template. Thereafter, the guide pin 184 remains inserted into the condyle 192 as illustrated in FIG. 9.

To form the cutout that removes the cartilage defect and receives the shaped allograft plug, a shaped drill bit, burr, or cutting disc can be employed. The shape and dimensions of the drill bit, burr or cutting disc, which will determine the shape and dimension of the formed cutout, may correspond to the allograft that is to be transplanted. An embodiment of such a drill bit 200 is illustrated in FIG. 10. Disposed along the central axis of the drill bit 200 is a tube or cannula 202 adapted to receive the guide pin. The drill bit 200 also includes a circular counter-bore forming element 204 and a conical-shaped cutting body 206 extending from the counter-bore forming element. The surface of the counter-bore forming element 204 and the cutting body 206 can include flutes or other suitable cutting structures. In other embodiments, to produce differently shaped cutouts, a different drill bit, burr, or cutting disc can be utilized. For example, referring to FIG. 11, there is illustrated a cannulated drill bit 210 having a circular counter-bore forming element 214 and a cylindrical cutting body 216.

In use, referring to FIG. 12, the conically cannulated drill bit 200 (or burr or cutting disc when used) is slid onto the guide pin 184 and placed proximate the host bone 190 such that the cutting body 204 is proximate the cartilage defect. The drill bit 200 can be rotated as indicated, either by hand or by a powered device, to cut into and remove the cartilage defect and the associated bone material thereby forming the cutout. Where desirable, lubrication can be supplied to facilitate cutting. Referring to FIG. 13, the shape of the cutout 220 formed into the host bone 190 will correspond to the shape of the drill bit used including having a conical void 222 and a circular counter bore 224 proximate the surface of the condyle 192. As will be appreciated, when the cannulated drill bit 210 illustrated in FIG. 11 is used, the formed cutout will have a corresponding shape including a circular counter-bore and a cylindrical void. In various embodiments, the shaped drill bits, burrs, and cutting disc can be used to make finishing cuts with different devices used to make initial cuts into the recipient site.

Figure 14:
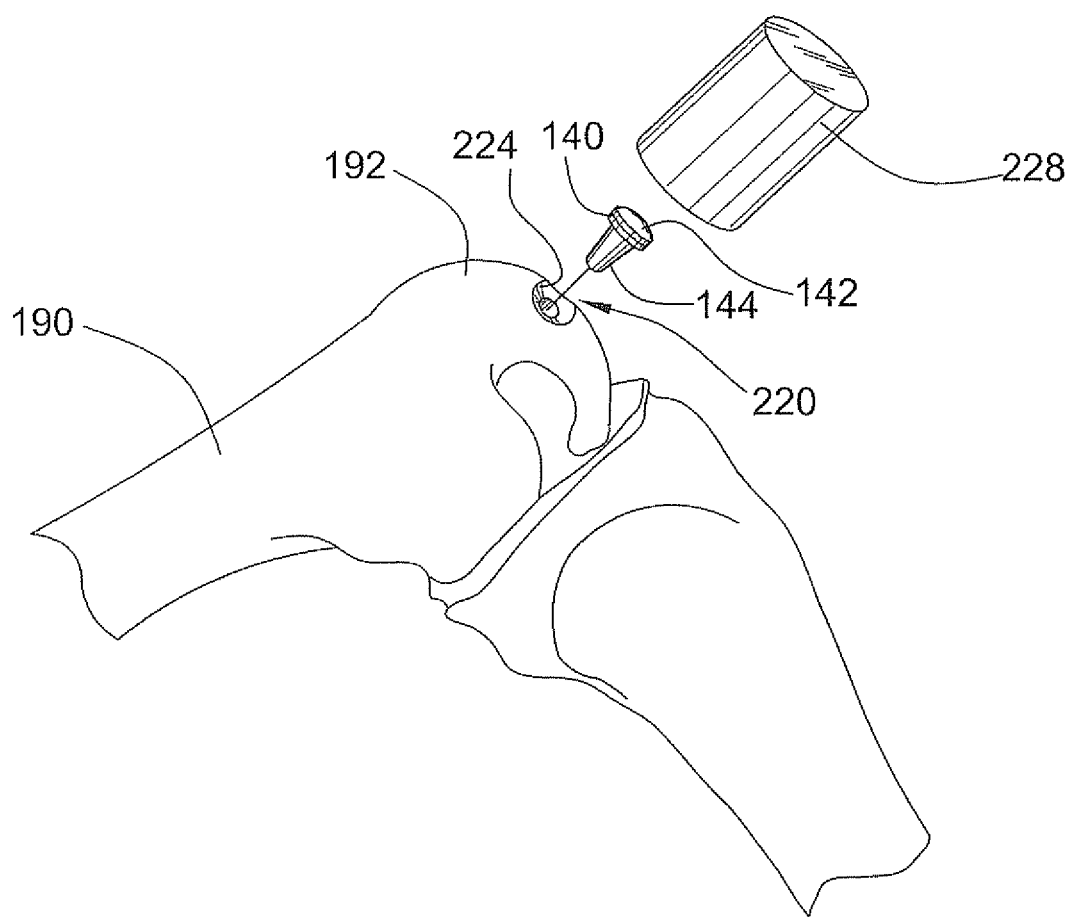
FIG. 14 is a perspective view of the condyle of a host bone illustrating a method of inserting an shaped allograft plug into a cutout formed at a recipient site using a tamp.

Referring to FIG. 14, a correspondingly shaped conical allograft plug 140 can be inserted into the shaped cutout 220 at the recipient site using a tamp 228 if necessary. Preferably, the allograft plug 140 and cutout 220 are sized to provide a close fit and, more preferably, a slight press fit, when engaged. Once properly inserted, the shaped cancellous stalk 144 is received deep into the cutout 220 and thus functions to anchor the allograft plug 140 to the host bone 190. Additionally, the cartilage plate 142 will be accommodated in the counter bore 224 such that the healthy cartilage of the allograft plug 140 aligns with the healthy cartilage on condyle 192 of the host bone 190. Overtime, the cancellous tissue and cartilage plate will permanently graft with the healthy bone tissue.

Figure 15:
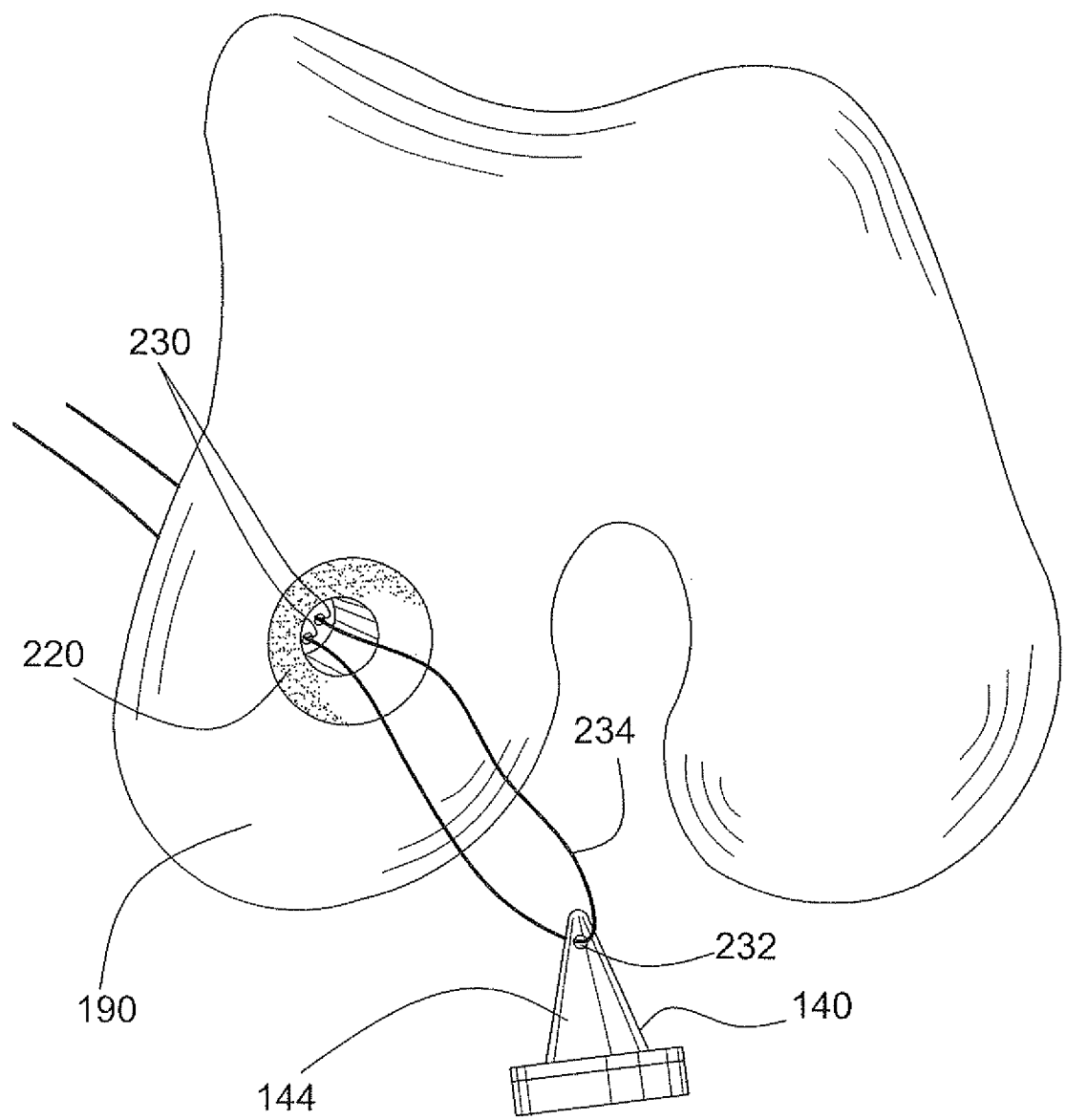
FIG. 15 is a front elevational view of the condyle of a host bone illustrating another method of inserting a shaped allograft plug into a cutout formed at a recipient site using a suture.

While inserting the allograft with a tamp is a common method, any other suitable method can be employed. For example, referring to FIG. 15, a method of implanting a conically shaped allograft plug 140 by the use of sutures is illustrated. According to the method, a pair of parallel holes 230 are cut into the outline of the cutout 220 and through to the opposite side of the host bone 190. A third hole 232 is cut transversely across the cancellous stalk 144 of the conical allograft plug 140. A flexible suture 234 or line can be run through the hole 232 in the cancellous stalk 144 with the ends of the suture run through holes 230 in the cutout 220 and out the opposite side of the host bone 190. As will be appreciated, pulling the ends of the suture 234 through holes 230 will draw the allograft plug 140 tightly into the cutout 220. It will be appreciated that any of the foregoing implantation procedures can work for any of the various shaped allograft plugs and corresponding cutouts.

Preparing the recipient site and removing and shaping an allograft plug for transplanting into the recipient site can occur simultaneously or, in some embodiments, the allograft plug can be removed and shaped in advance of preparing the recipient site. Moreover, the preparation of an allograft plug can occur at a different location than the where the insertion of the allograft plug is to occur. To preserve an allograft plug prior to insertion, the allograft plug can be cryogenically preserved. This is an alternative to preparing and transplanting a fresh allograft plug.

Figure 16:
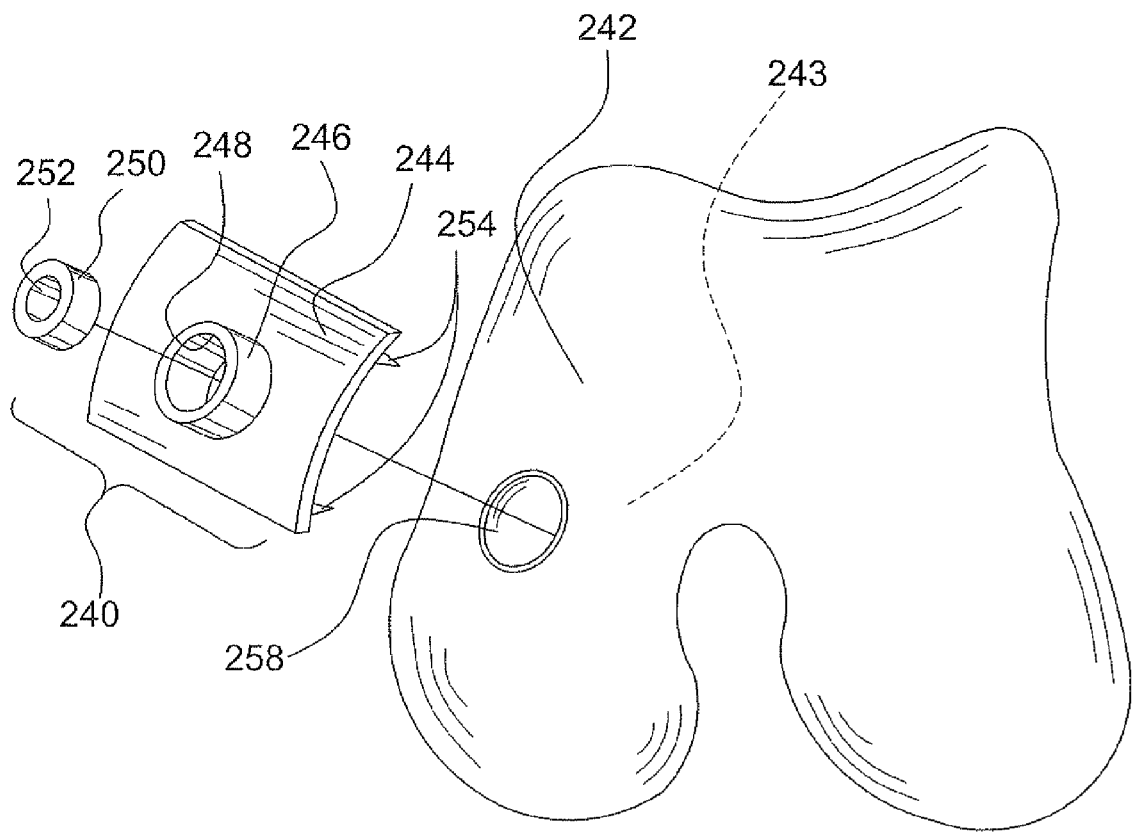
FIG. 16 is a perspective view of a guide plate with a removable guide cylinder for assisting in removing and shaping a cylindrically shaped allograft plug from a donor bone.

Though the foregoing procedures for preparing and transplanting a shaped allograft plug can be conducted with any common medical instruments, in a further aspect of the invention, various special instruments and tools, in addition to the template and the shaped drill bit, burr, or cutting discs, are provided. For example, to produce the shaped allograft plug illustrated in FIG. 2 from a donor bone, a guide plate 240 as illustrated in FIG. 16 can be used to guide various crown saw cuts into a donor bone 242. The guide plate includes a generally rectangular base plate 244 that is curved or cambered to fit on a condyle of the donor bone and from one surface of which projects a circular guide cylinder 246. The guide cylinder 246 defines a hollow bore 248 of a first diameter that is disposed through the base plate 244. Slidably receivable in the guide cylinder 246 is a smaller second guide cylinder 250 through which is disposed a second hollow bore 252 of a second, smaller diameter. The guide plate 240 also includes a plurality of short sharp teeth 254 projecting from a surface of the base plate 244 opposite the guide cylinder 246.

Figure 2:
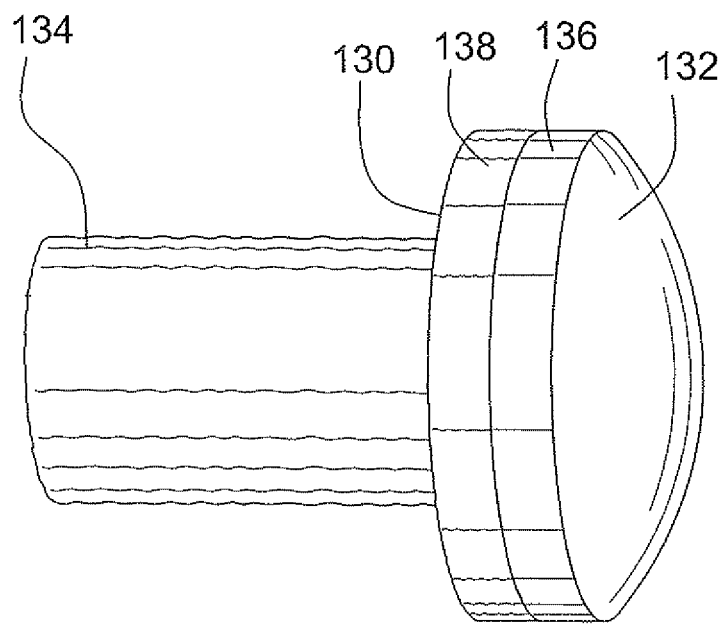
FIG. 2 is a perspective view of an allograft plug shaped in accordance with an embodiment of the invention, the allograft plug having a cartilage plate and a cylindrical cancellous stalk.

In use, the guide plate 240 with the second guide cylinder 250 inserted is attached to the donor bone 242 on a surface diametrically opposite of the donor site 243. The teeth 254 help attach the guide plate to the donor bone 242 and can be inserted into the donor bone by thumb pressure or a light tamp. To produce a first cut into the donor bone 242, a tubular crown saw having a diameter slightly less than diameter of the second hollow bore 252 of the guide plate 240 is inserted through the second hollow bore and into the donor bone. Preferably, the first cut is made into the donor bone 242 from the location of the guide plate 240 opposite the donor site 243 to a point a proximate the cartilage plate of the donor site and more preferably only a few millimeters from the cartilage plate. The second, smaller guide cylinder 250 is then removed from the guide plate 240. A second crown saw, larger than the first crown saw but with a diameter adapted to be slidably received into the first hollow bore 248 of the guide plate 240 is inserted through the first hollow bore and across the donor bone 242, thereby detaching a portion of bone tissue 258 from the donor bones The detached bone tissue can then be trimmed to a desired length, for example, as measured from the cartilage plate to the cancellous tissue, to produce the allograft plug 130 having the cylindrical cancellous stalk 134 as illustrated in FIG. 2. Hence, the guide plate helps avoid injury to adjacent normal cartilage on the donor bone. Furthermore, the guide plate 240 can be used in conjunction with a clamping device of the type illustrated and described with respect to FIG. 1. In other embodiments, the guide plate 240 can be used with only the first guide cylinder 246 and the second, larger diameter crown saw to produce a cylindrical allograft plug that can be subsequently shaped.

Figure 17:
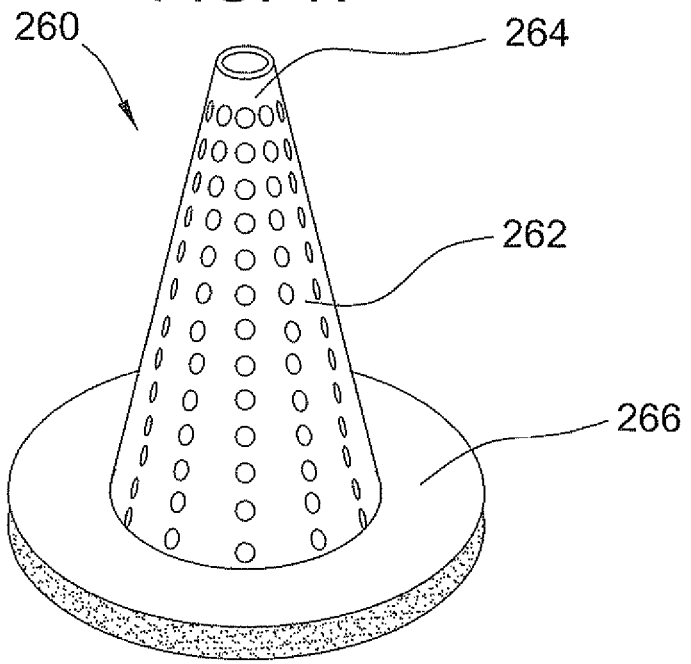
FIG. 17 is a top perspective view of a cannulated burring shell for removing cancellous material and shaping a conically shaped allograft plug.

To produce an allograft plug having a conical shaped cancellous stalk, as illustrated in FIG. 3, a cannulated burring shell can be used in conjunction with a specially adapted sleeve to further remove cancellous tissue from an allograft plug having a cylindrically—shaped stalk. Referring to FIG. 17, the cannulated burring shell 260 has a hollow conical shell body 262 with a guide aperture 264 disposed through the tip of the cone to provide the cannulated feature. The cannulated burring shell 264 can also include a circular burring disk 266 that extends annularly outward from the base of the conical shell body 262. The interior surface of the conical shell body 262 and the underside of the burring disc 266 are adapted to grate or remove cannellous bone tissue.

Figure 18:
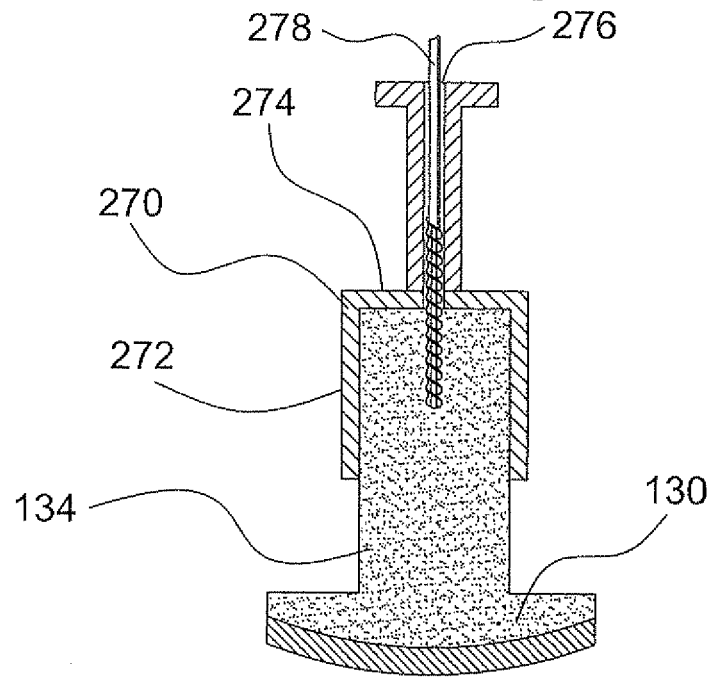
FIG. 18 is a cross-sectional view of a sleeve placed about an allograft plug having a cylindrical shaped cancellous stalk and a guide pin inserted through the sleeve and partially into the cancellous stalk.

In order to utilize the cannulated feature of the burring shell to facilitate proper shaping of the conical stalk, referring to FIG. 18, the specially adapted sleeve 270 is first placed about the cylindrical allograft plug 130. The sleeve 270 includes a tubular sleeve body 272 and a base plate 274 having a centrally located guide aperture 276 disposed therein. The sleeve 270 is placed about the allograft plug 130 such that the tubular sleeve body 272 receives the cylindrical cancellous stalk 134. Another elongated guide pin 278 is inserted through the guide aperture 276 and partially into the cancellous tissue of the stalk 134 as illustrated. Due to the concentric relation of the guide aperture and the tubular sleeve body 272, the guide pin 278 will be concentrically aligned within the cancellous stalk. The sleeve 270 can then be removed and the cannullated burring shell 260 of FIG. 17, via its guide aperture 264, slide onto the guide pin so that the shell body 262 aligns with the cylindrical cancellous stalk. As can be appreciated, rotation of the cannulated burring shell 260 will remove cancellous tissue from the stalk and thereby form the conical shape. Furthermore, the burring disk 266 can remove or smooth the cancellous tissue on the underside of the allograft plug cartilage plate.

Figure 19:
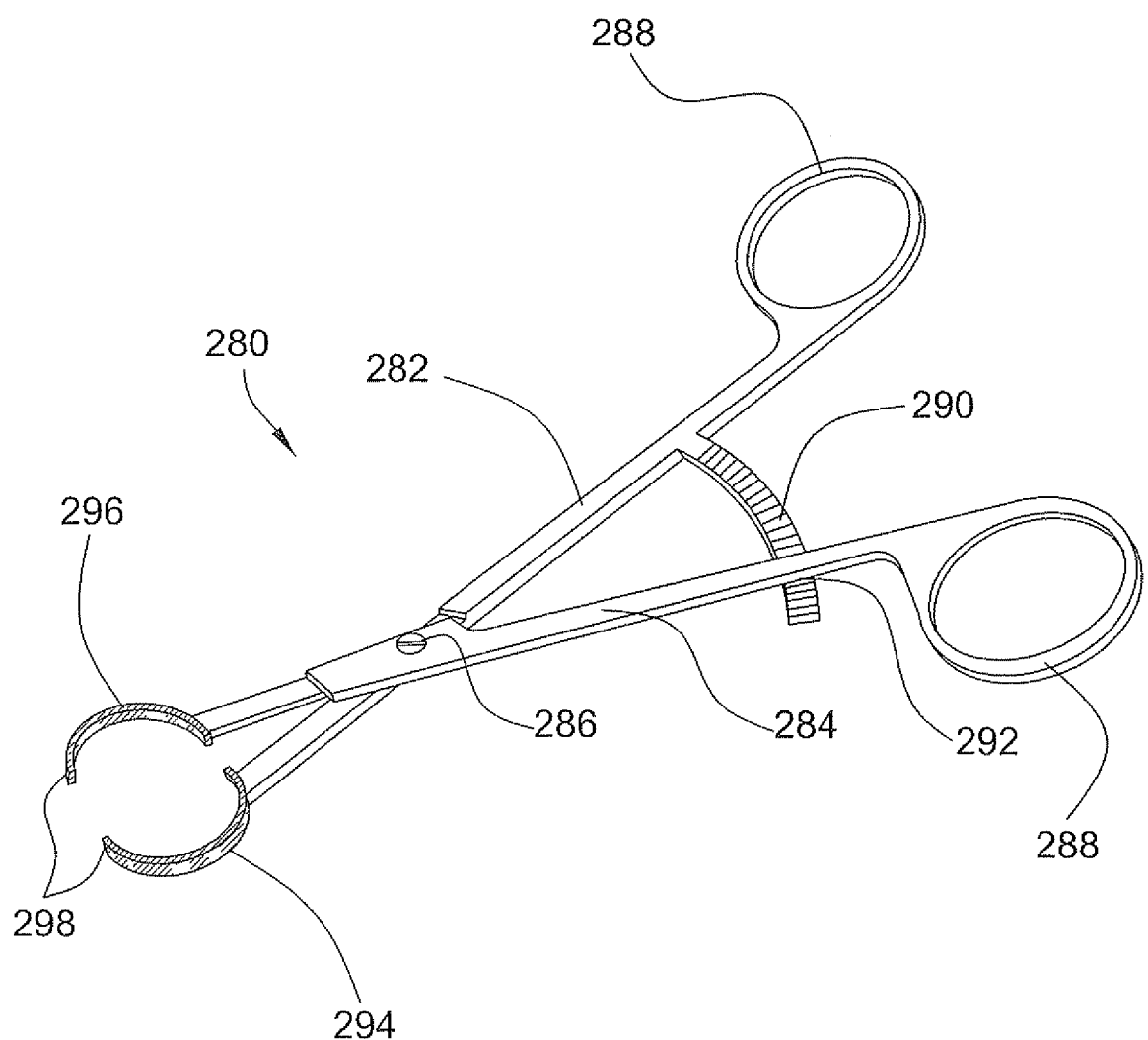
FIG. 19 is a perspective view of a pair of specially configured forceps for handling and manipulating a shaped allograft plug.

To handle a shaped allograft plug, especially a cylindrically or conically shaped plug, a pair of specially configure forceps can be provided. Referring to FIG. 19, the forceps 280 can include first and second lever arms 282, 284 that intersect and are pivotally joined at a pivot point 286. To grasp and manipulate the forceps, there is formed at the proximal end of each lever arm an eyelet 288 that can accommodate an operators fingers. Traversing the first lever arm 282 is a locking arm 290 that can engage a locking mechanism 292 on the second arm 284 so as to control and fix articulation of the forceps 280. The forceps 280 can be made from any suitable material such as, for example, stainless steel.

Formed at the working ends of the first and second lever arms 282, 284 are curved or semicircular clamps 294, 296. The clamps 294, 296 can be joined to the respective lever arms 282, 284 at any suitable angle such as, for example, in-line with the lever arms or at right angles with the lever arms. To prevent damaging the allograft plug, a suitable soft material 298 such as an elastomer can be coated onto the clamps 294, 296. Preferably the elastomer material can be silicone rubber. Hence, when handling a cylindrical or conical allograft plug, the curved clamps 294, 296 can be placed around the cartilage plate or cancellous stalk with the elastomer 298 protecting the bone tissue.

Figure 20:
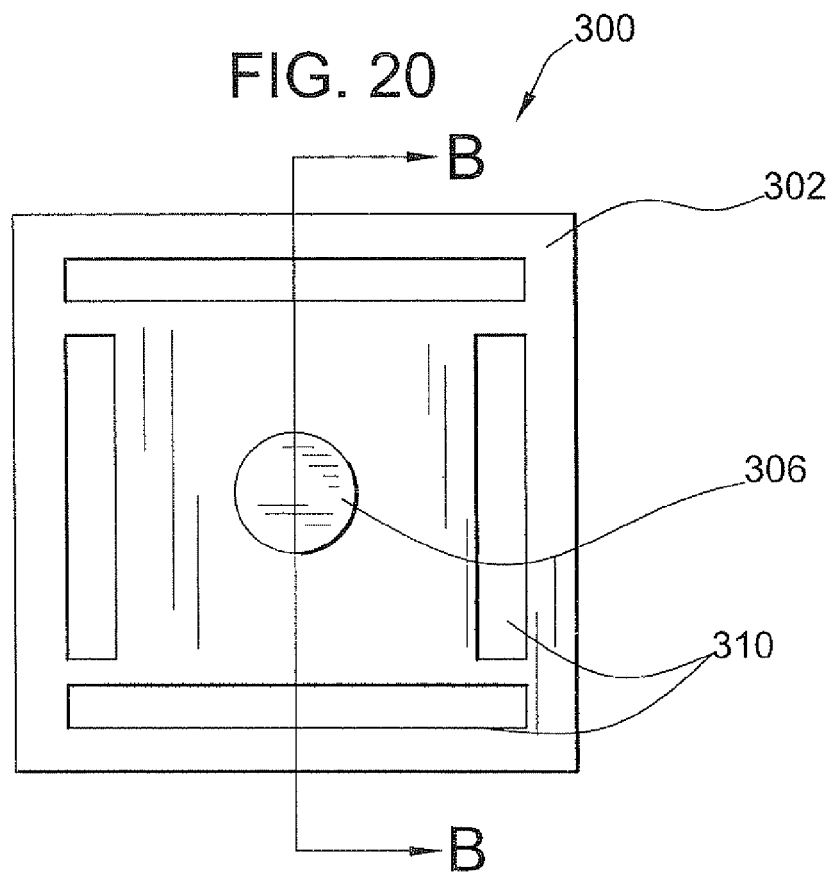
FIG. 20 is a front elevational view of a template having cut slots for removing and shaping a rectilinear allograft plug from a donor bone.
Figure 21:
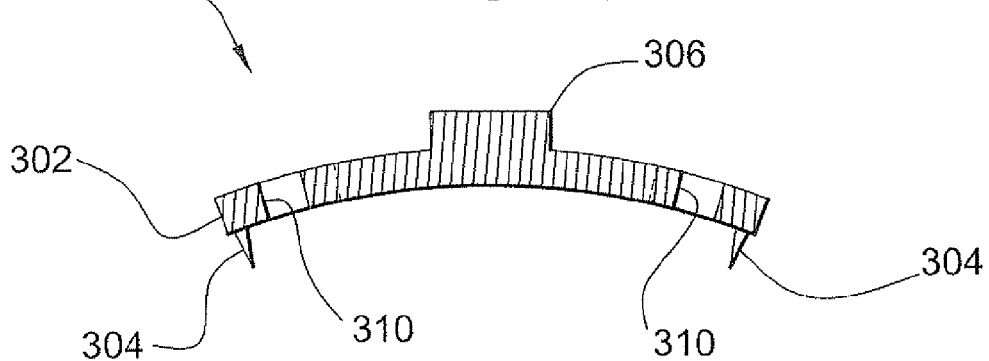
FIG. 21 is a cross-sectional view of the template taken along line B-B of FIG. 20.

To produce a rectilinear shaped allograft plug, such as the rectangular plug illustrated in FIG. 4, a special template 300 as illustrated in FIGS. 20 and 21 can be used. The template 300 includes a plate 302 having a cambered or curved shaped to adapt the plate for attachment to the condyle surface of a donor bone. Protruding from one surface of the plate 302 are a plurality of sharp teeth 304 to assist in attaching the template to the donor bone. The template 300 can further include an engagement structure 306 on the plate surface opposite the protruding teeth 304 to engage a detachable handle as described above. Furthermore, while the illustrated template 300 has a rectangular shape, in other embodiments the template can have other suitable shapes depending upon the shape of the allograft plug desired.

To actually remove the allograft plug, there is disposed through the plate 302 and within the perimeter outlined by the sharp teeth 304 a plurality of elongated cut slots 310 that are adapted to accommodate a osteotome, chisel, oscillating saw, or other cutting device. To produce a rectangular allograft plug, the illustrated cut slots 310 are arranged rectangularly. However, in other embodiments, to produce other shaped allograft plugs, such as triangular, the cut slots can be arranged in other patterns, such as triangularly. The cut slots 310 are furthermore disposed into the template 300 on a converging angle such that, when a cutting device is inserted through the cut slots and into the donor bone, the cuts being made will intersect at a point in the cancellous bone tissue. Intersecting the cuts will detach the allograft plug from the donor bone and simultaneously shape the allograft plug and its cancellous stalk. Hence, locating the cut slots 310 within the outline of the teeth 304 enables insertion of the teeth into the donor bone without damaging the healthy cartilage on allograft plug.

Figure 22:
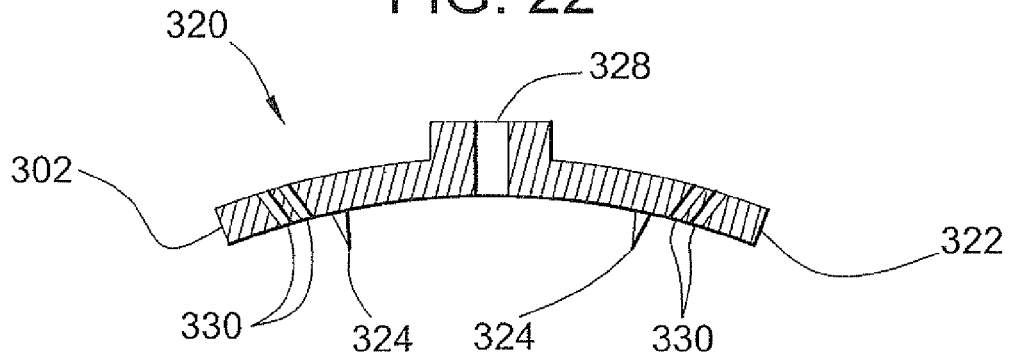
FIG. 22 is a cross-sectional view of another embodiment of a template, similar to the template shown in FIGS. 20 and 21, but adapted for preparing a recipient site on a host bone to receive a rectilinear allograft plug.

To prepare a recipient site for receiving an rectilinear allograft plug, a template 320 as illustrated in FIG. 22 can be used. The plate 322 of the template 320 is similar in shape and configuration to the template 300 of FIGS. 20 and 21 and also includes a plurality of cut slots 330 disposed angularly therethrough. To form a cutout in the host bone, the template 320 can be attached to the host bone at a location corresponding to a cartilage defect by utilizing the sharp teeth 324 protruding from the plate 322. To avoid damaging healthy cartilage on the host bone, the cut slots 330 are preferably located outside of the outline of the teeth 324. After attachment, various suitable cutting devices can be inserted through the cut slots 330 and into the donor bone to form the cutout. In an embodiment, to enable installation of the guide pin into the recipient site for aligning subsequent operations, the template 320 can have a guide aperture 328 disposed through the plate 322 generally central of teeth 324 and the cut slots 330.

As will be appreciated from the foregoing, the procedures and instruments described may also be applicable to the preparation and transplantation of a shaped autograft plug. For example, the removal, shaping, and insertion of an autograft plug from a host site and into a recipient site within the same patient is readily applicable with respect to rectilinear autograft plugs and can be performed using the same instruments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying Out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A system for preparing a recipient site on a host bone comprising:
   an osteochondral allograft;
   a template including a plate having a first surface and a second surface generally parallel to the first surface, a plurality of sharp teeth protruding from the first surface, an engagement structure protruding from the second surface, and a centrally disposed guide aperture;
   an elongated guide pin adapted to be received in the guide aperture;
   a cannulated drill bit, burr, or cutting disk adapted to receive the guide pin within a cannula thereof and slide onto the guide pin, and including a cutting body extending from a circular counter-bore forming element at a proximal end of the cannulated drill bit, burr, or cutting disk, the circular counter-bore forming element including first cutting members extending towards the cutting body; and
   a detachable handle detachably engageable with the engagement structure such that when engaged, the handle extends from only the second surface of the template, the handle disposed along an axis of the guide aperture so as to be configured to receive the guide pin through the handle when the guide pin is inserted through the guide aperture.

2. The system of claim 1, wherein the cutting body is cylindrical or conical.

3. The system of claim 1, wherein the detachable handle detachably engages the engagement structure by a twist lock mechanism.

4. The system of claim 1, wherein the detachable handle extends generally perpendicularly to the second surface.

5. The system of claim 1, wherein each one of the plurality of teeth is arcuately shaped and extends arcuately in a lengthwise direction such that each one of the teeth is located on the circumference of a common circle, the plurality of teeth including two opposed pairs of teeth spaced equidistant along the common circle.

6. A system for preparing a recipient site on a host bone comprising:
   an osteochondral alloqraft;
   a template comprising a plate having a generally circular perimeter, the plate having a first surface, a plurality of arcuately shaped teeth protruding from the first surface arranged in a circular pattern concentric with the plate, each one of the plurality of arcuately shaped teeth extending arcuately in a lengthwise direction such that each one of the teeth is located on the circumference of a common circle, the plurality of arcuately shaped teeth including two opposed pairs of teeth spaced equidistant along the common circle, and a centrally disposed guide aperture;
   an elongated guide pin adapted to be received in the guide aperture;

a handle defining a handle aperture extending therethrough and configured to detachably couple with the template, the handle aperture is aligned with the guide aperture to accommodate simultaneous passage of the guide pin through the handle aperture and the guide aperture when the handle is coupled to the template; and a cannulated drill bit, burr, or cutting disk, the cannulated drill bit, burr or cutting disk adapted to slide onto the guide pin.

7. The sysytem of claim 6, wherein the cannulated drill bit, burr or cutting disk has a counterbore forming element at a proximal end and a cutting body extending from the counterbore forming element.

8. The system of claim 7, wherein the cutting body is cylindrical or conical.

9. The system of claim 6, wherein the plate has a second surface generally parallel to the first surface, the second surface having an engagement structure protruding therefrom.

10. The system of claim 9, wherein the detachable handle is detachably engaged with the engagement structure protruding from the second surface such that when engaged, the handle extends from only the second surface.

11. The system of claim 10, wherein the detachable handle detachably engages the engagement structure by a twist lock mechanism.

12. The system of claim 6, wherein the plate has a second surface generally parallel to the first surface and an engagement structure protruding from the second surface, wherein the handle detachably engages the engagement structure, the detachable handle having a first terminal end and a second terminal end, with the detachable handle's first terminal end terminating at the engagement structure when detachably engaged with the engagement structure, and the detachable handle's second terminal end extending therefrom.

13. The system of claim 12, wherein the detachable handle detachably engages the engagement structure by a twist lock mechanism.

14. The system of claim 13, wherein the detachable handle extends generally perpendicularly to the second surface.

15. The system of claim 6, wherein the cannulated drill bit, burr or cutting disk is adapted to receive the guide pin within a cannula thereof and slide onto the guide pin; and wherein the cannulated drill bit, burr, or cutting disk includes a cutting body extending from a circular counter-bore forming element at a proximal end of the cannulated drill bit, burr, or cutting disk, the circular counter-bore forming element including a plurality of first cutting members extending towards the cutting body.

16. A system for preparing a recipient site on a host bone comprising:

an osteochondral allograft;

a template including a plate having a circular perimeter, the plate having a first surface and a second surface parallel to the first surface, a plurality of teeth protruding from the first surface arranged in a circular pattern concentric with the plate, an engagement structure protruding from the second surface, and a centrally disposed guide aperture;

an elongated guide pin adapted to be received in the guide aperture;

a cannulated drill bit, burr, or cutting disk, the cannulated drill bit, burr or cutting disk adapted to slide onto the guide pin to prepare a recipient site; and a detachable handle detachably engageable with the engagement structure such that when engaged, the detachable handle extends from only the second surface of the template, the handle defining a handle aperture that is axially aligned with the guide aperture of the template when the handle is attached to the template, the handle aperture and the guide aperture are configured to simultaneously receive the elongated guide pin therethrough.

17. The system of claim 16, wherein the detachable handle detachably engages the engagement structure by a twist lock mechanism.

18. The system of claim 16, wherein the cannulated drill bit, burr or cutting disk has a counterbore forming element at a proximal end and a cutting body extending from the counterbore forming element.

19. The system of claim 18, wherein the cutting body is cylindrical or conical.

20. The system of claim 16, wherein the detachable handle extends generally perpendicularly to the second surface.

21. The system of claim 16, wherein the cannulated drill bit, burr or cuffing disk is adapted to receive the guide pin within a cannula thereof and slide onto the guide pin; and wherein the cannulated drill bit, burr, or cutting disk includes a cutting body extending from a circular counter-bore forming element at a proximal end of the cannulated drill bit, burr, or cutting disk, the circular counter-bore forming element including a plurality of first cutting members extending towards the cutting body.

22. The system of claim 16, wherein each one of the plurality of teeth is arcuately shaped and extends arcuately in a lengthwise direction such that each one of the teeth is located on the circumference of a common circle, the plurality of teeth including two opposed pairs of teeth spaced equidistant along the common circle.

* * * * *

UNITED STATES PATENT AND TRADEMARK OFFICE
CERTIFICATE OF CORRECTION

Page 1 of 1

PATENT NO. : 8,882,774 B2
APPLICATION NO. : 11/677414
DATED : November 11, 2014
INVENTOR(S) : Theodore I. Malinin It is certified that error appears in the above-identified patent and that said Letters Patent is hereby corrected as shown below:

In the Specification

Column 4, line 4; Delete "condyle" and insert --donor site--.

In the Claims

Column 10, line 54, claim 6; delete "alloqraft" and insert --allograft--.

Column 12, line 36, claim 21; delete "cuffing" and insert --cutting--.

Signed and Sealed this
Twenty-first Day of April, 2015

Michelle K. Lee
*Director of the United States Patent and Trademark Office*